United States Patent [19]

Duchek

[11] Patent Number: 5,312,970
[45] Date of Patent: May 17, 1994

US005312970A

[54] METHOD OF PREPARING D-PROPOXYPHENE

[75] Inventor: John R. Duchek, St. Louis, Mo.

[73] Assignee: Mallinckrodt Specialty Chemicals Company, Chesterfield, Mo.

[21] Appl. No.: 853,847

[22] Filed: Mar. 19, 1992

Related U.S. Application Data

[63] Continuation of Ser. No. 700,328, May 9, 1991, abandoned, which is a continuation of Ser. No. 357,564, May 26, 1989, abandoned.

[51] Int. Cl.$^5$ .............................................. C07C 67/02
[52] U.S. Cl. ..................................................... 560/250
[58] Field of Search ......................................... 560/250

[56] References Cited

U.S. PATENT DOCUMENTS

| | | | |
|---|---|---|---|
| 2,728,779 | 12/1955 | Pohland | 560/250 |
| 3,065,261 | 11/1962 | Stephens | 560/250 |
| 3,487,469 | 12/1969 | Marxer | 560/250 |
| 3,728,379 | 4/1973 | Stephens | 560/250 |
| 4,661,625 | 4/1987 | White | 560/250 |

FOREIGN PATENT DOCUMENTS

| | | | |
|---|---|---|---|
| 1568252 | 1/1973 | Fed. Rep. of Germany | 560/250 |
| 1793640 | 4/1973 | Fed. Rep. of Germany | 560/250 |
| 15441 | 9/1978 | Hungary . | |

OTHER PUBLICATIONS

Pohland and Sullivan, J. Am. Chem. Soc. 75:4458–4461 (1953).
Pohland and Sullivan, J. Am. Chem. Soc. 77:3400–3401 (1953).
Pohland, Peters, and Sullivan, J. Organic Chem. 28:2483–2484 (1963).

Primary Examiner—José G. Dees
Assistant Examiner—Joseph M. Conrad
Attorney, Agent, or Firm—Rothwell, Figg Ernst & Kurz

[57] ABSTRACT

D-propoxyphene can be prepared by reacting d-oxyphene and propionic anhydride. Preferably, an excess of propionic anhydride is used. The reaction easily proceeds at temperatures of 70° to 80° C. and produces yields exceeding 95 percent of theory. The free base d-propoxyphene can easily be converted in high yields to its hydrochloride or napsylate salts, both analgesics.

22 Claims, No Drawings

METHOD OF PREPARING D-PROPOXYPHENE

This is a continuation of application Ser. No. 07/700,328, filed May 9, 1991, now abandoned, which was a continuation of application Ser. No. 07/357,564 filed May 26, 1989, now abandoned.

FIELD OF THE INVENTION

This invention relates to the preparation of d-propoxyphene, an analgesic, and its hydrochloride and napsylate salts.

BACKGROUND OF THE INVENTION

Of the many phenylpropylamines which show analgesic activity, the two most important are methadone and propoxyphene. The optically active alpha-dextro stereoisomer of propoxyphene is the only stereoisomer of propoxyphene which possesses analgesic properties. It is commonly used in its hydrochloride salt form which is a bitter, white crystalline powder freely soluble in water and soluble in alcohol. Its chemical name is α-d-1,2-diphenyl-2-propionoxy-3-methyl-4-dimethylaminobutane hydrochloride and is sold under several different trademarks including, for example, DARVON, DOLENE, and SK-65. The napsylate salt, i.e., the naphthalene sulfonate, is also used in many drug forms. It has previously been made from the hydrochloride salt.

Preparation of d-propoxyphene hydrochloride was first described by A. Pohland and H. R. Sullivan at J. Am. Chem. Soc., Volume 75, pp. 4458(1953). Therein, the authors disclosed a synthesis involving several stages, (1) preparation of an aminoketone called β-dimethylaminobutrophenone by addition of the secondary amine to phenylpropenyl ketone; (2) a Grignard reaction of the amino ketone with benzylmagnesium chloride to yield the amino, hydrochloride-carbinols described as α-(75%) and β-(15%) 4-dimethylamino-1,2-diphenyl-3-methyl-2-butanol hydrochloride (sometimes hereinafter referred to as d-oxyphene hydrochloride); and (3) acylation of the α-amino carbinol hydrochloride by addition of an equal weight of propionic anhydride and five times that weight of pyridine and heating to reflux for several hours. Note the following reaction formula:

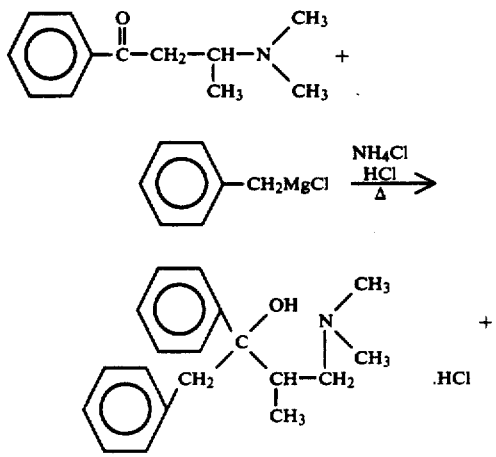

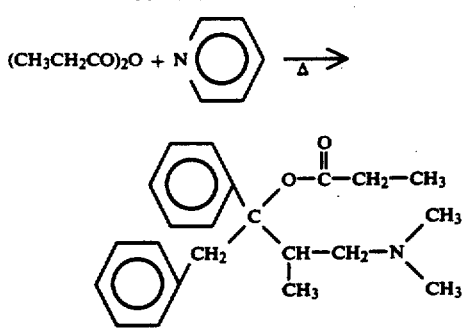

After cooling to recover the crude product, it was purified by two recrystallizations from methanol-ethyl acetate solution resulting in a yield of 70%.

Although this work confirmed that the α and not the β-diastereoisomers of propoxyphene gave rise to analgesic activity, it was still necessary to determine which of the optical forms of the α-diastereoisomer, i.e. α-d(+) or α-l(−), was responsible for the analgesic activity. Accordingly, Pohland and Sullivan reported in the J. Am. Chem. Soc., Volume 77, pp. 3400 (1955) their work on resolution of α-dl-4-dimethylamino-1,2-diphenyl-3-methyl-2-butanol by fractional crystallization of its d-camphorsulfonic acid salt. From the respective α-d and α-l carbinol d-camphorsulfonic salts the optically active hydrochloride salts were prepared. The α-d-hydrochloride was acylated using propionic anhydride and triethylamine, while the α-l hydrochloride was acylated using propionic anhydride and pyridine. It was therein found that only the α-d stereoisomer gave the analgesic response. However, final purification of the hydrochloride salt required additional HCl and three recrystallizations and with yields of less than about 70%.

In 1963, Pohland, Peters and Sullivan reported in the J. Org. Chem., Vol. 28, pp. 2483, an alternative synthetic route for α-d-propoxyphene hydrochloride. Working backwards from the desired optically active isomer of propoxyphene by its hydrolysis and dehydration to stilbene, followed by ozonization of the stilbene, the authors discovered good yield of (−)-β-dimethylamino-α-methylpropiophenone. This optically active amino ketone was found to be surprisingly stable in salt form thus permitting its use as a starting material for a stereo selective synthesis of α-d-propoxyphene. Racemic β-dimethylamino-α-methylpropiophenone was resolved by crystallization of the dibenzoyl tartrate salts from acetone solution. The use of dibenzoyl-(−)-tartaric acid yielded the insoluble salt having (−)-β-dimethylamino-α-methylpropiophenone, while the use of the (+) tartaric acid yielded the salt having the (+) amino ketone isomer.

It is of interest that according to this reported synthesis, it was the (−) isomer of β-dimethylamino-α-methylpropiophenone, which when liberated from its (−) tartrate salt by Grignard reaction with benzylmagnesium chloride provided good yields of the (+) or (d) isomer α-1,2-diphenyl-3-methyl-4-dimethylamino-2-butanol which of course is the carbinol precursor for α-d-propoxyphene. The reported yields were 69%. The acylation was accomplished as had been previously reported, i.e., by means of propionic anhydride in either triethylamine or pyridine.

In 1978, Hungarian Pat. No. 14,441 disclosed a synthesis of α-d-propoxyphene employing the above-described method except that (1) the (+) tartaric acid was employed in the resolution of the racemic β-dimethylamino-α-methylpropiophenone and (2) the acylation was accomplished by reacting triethylamine in chloroform, propionyl chloride and the carbinol rather than propionyl anhydride and the carbinol hydrochloride. Still the product was precipitated in ether and required an amine catalyst.

Most recently, U.S. Pat. No. 4,661,625 disclosed a synthetic method involving acylation of the carbinol (d-oxyphene) with propionyl chloride and thionyl chloride in dichloromethane. The yield of d-propoxyphene hydrochloride was improved to at least 76%, but use of the toxic additive thionyl chloride was required to get to that level. In addition, methylene chloride or another chlorinated solvent was required. Chlorinated impurities resulted and caused difficulties in purification.

However, a method that provides even higher yields of d-propoxyphene and its salts and doesn't require toxic and/or hazardous additives and solvents has long been highly desired. It is an object of the present invention to provide a means of producing d-propoxyphene in high yields without the need for amines or chlorinated solvents. It is a further object to provide methods of producing the hydrochloride and napsylate salts of d-propoxyphene in higher yields than previously obtainable.

SUMMARY OF THE INVENTION

D-propoxyphene is prepared by acylation of the free base carbinol, d-oxyphene, using propionic anhydride. Surprisingly, no additional solvent is needed. D-oxyphene is sufficiently soluble in propionic anhydride to react with it, but the reaction is less exothermic than expected so no additional solvent is required to dissipate the heat released and achieve sufficient temperature control to accomplish the acylation. Catalysts, preferably bases, may be used to increase the rate, but reaction times can be kept within acceptable limits without them. Surprisingly, water will increase the rate of reaction and may be present or deliberately added to the reaction mixture.

D-propoxyphene prepared by this method may be directly converted to the napsylate salt without previous conversion to the hydrochloride salt. This has the advantage of greatly increasing the efficiency of the preparation and the yield of the napsylate salt.

The present invention also provides a method of preparing the hydrochloride salt of d-propoxyphene free base using relatively inexpensive reactants. Higher overall yields result from the improved yields achieved in the acylation step.

DETAILED DESCRIPTION AND PREFERRED EMBODIMENTS

D-oxyphene is well-known in the art and can be derived from any of several prior art methods, including those hereinbefore described, and is available commercially. In accordance with this invention, d-oxyphene may be reacted directly with propionic anhydride under acylating conditions requiring no amine or other additive and no chlorinated solvent. Although the reaction can proceed with equimolar amounts of d-oxyphene and the anhydride, it is preferred to use an excess of anhydride to act as the solvent and to drive the acylation reaction to completion. It is preferred to use at least 2.0 moles anhydride per mole of d-oxyphene. More preferably, a ratio of from 2.2 to 2.3 moles propionic anhydride per mole d-oxyphene is used. Less than an equimolar amount of propionic anhydride would yield d-propoxyphene, but the excess d-oxyphene will cause recovery and purification problems.

The solution of d-oxyphene in propionic anhydride is preferably heated in a nitrogen atmosphere. The temperature can range between about 50° and about 120° C., preferably between 70° and 80° C. Higher temperatures (above 90° C.) may promote formation of impurities.

The reaction time can vary according to the temperature employed, but will generally be between 2 and 10 hours, preferably 4 to 6 hours at the preferred temperatures.

Surprisingly, it has been found that water can increase the rate of the reaction. When present in a catalytic amount, about 0.2–0.4 moles per mole of d-oxyphene, a two-fold increase in the reaction rate has been observed. It is theorized that general base catalysis of the acylation reaction occurs before the water hydrolyzes propionic anhydride. Water may, therefore, be present during the reaction, and it may be preferable to add water to the reaction.

After the reaction is complete, the free base form of d-propoxyphene may be isolated in the usual manner. The preferred method is by precipitation from water or an ethanol-water mixture. Unreacted propionic anhydride is converted in water to propionic acid. This quenches the reaction. This acid, combined with the propionic acid produced by the acylation reaction, lowers the pH of the mixture and keeps the d-propoxyphene in solution. When the pH is raised to about 8.8 to 9.0, the free base will precipitate and can be recovered at greater than 95 percent yields. Ammonium hydroxide or other water soluble bases, such as sodium hydroxide or potassium hydroxide, can be used to raise the pH.

Purity of the recovered d-propoxyphene prepared by the present method is very good. It can be checked by nuclear magnetic resonance analysis or by liquid chromatography. It is highest when a mixture of ethanol and water is used to quench the propionic acid and anhydride reaction mixture. Ethanol helps keep any minor impurities in solution and produces the highest purity. This may occur due to formation of ethyl propionate which may have an increased solvent effect.

When ethanol it used, it should be washed from the recovered d-propoxyphene. This is preferably done by washing with deionized water, more preferably followed by reslurrying with additional washings in deionized water.

Once d-propoxyphene as the free base is recovered, it can be dried and stored for a time in this state. It can be converted to the hydrochloride salt or the napsylate salt before storage stability is of concern.

The present invention also includes the method of converting the free base to the hydrochloride salt. As the previous methods of preparation produced the hydrochloride salt without isolating the free base, an efficacious method of converting the free base to the hydrochloride salt had to be devised. It was found that the dried free base should be dissolved in ethyl acetate, which is then mixed with methanolic hydrogen chloride (methanol in which anhydrous HCl has been dissolved). It is preferred to use a molar equivalent of HCl. The hydrochloride salt precipitates from this mixture. Higher yields can be obtained by recycling the mother liquor, but good overall yields can be achieved without it due to the greatly improved yield in the acylation reaction.

The napsylate salt can be prepared from the hydrochloride salt by known methods. However, it has been found that the napsylate salt of d-propoxyphene can be prepared directly from the free base without completely drying it. After isolation, preferably by precipitation as described above, the free base solids are filtered to remove most of the water. Then the base is reslurried in water and one equivalent of hydrochloric acid is added. Sodium 2-naphthalene sulfonate (hereinafter called sodium napsylate) is added with ethanol. Preferably a slight molar excess of sodium napsylate is used, for example 1.1 moles per mole of free base. From this mixture d-propoxyphene napsylate may be crystallized. It is preferably washed and dried to the monohydrate state.

This procedure greatly improves the yield of the napsylate salt because the acylation step achieves high yields and losses inherent in the isolation of the hydrochloride salt are avoided.

The following examples are offered by way of illustration and are not limiting.

EXAMPLE 1

To a 5-liter flask equipped with an overhead stirrer, a nitrogen feed, thermometer, and heating mantle was added 2.0 kg (7.06 moles) d-oxyphene purchased from Merrell-Dow. To this was added 2.0 L (15.6 moles) propionic anhydride (Aldrich) with stirring and heating. The temperature was raised to 75°-80° C. over 35 minutes and maintained at no more than 81° C. for four hours. The mixture was cooled to room temperature and then added dropwise to 10.0 L deionized water over 30 minutes. A clear yellow solution resulted. 1.85 L ammonium hydroxide was added to raise the pH to 8.8. Seed crystals of d-propoxyphene were added and white solids precipitated. The solution and precipitate were chilled by immersion in ice bath and filtered. The solid was dried by vacuum and then placed in a 60° C. oven for 2 days. The yield was 2390 g of white crystals, 99.7% of theory.

EXAMPLE 2

To a 22-liter vessel equipped with a stirrer, heating mantle, thermometer and a nitrogen feed was added 5.0 kg (17.6) moles d-oxyphene (Merrell-Dow). To it was added 5.0 L (39.0 moles) propionic anhydride (Eastman-Kodak). The temperature was raised and varied from 73°-88° C. over 4¼ hours. The reaction mixture was split into two parts, each about 5 L, and each was treated as follows: The mixture was slowly added to a mixture of 3.125 L absolute ethanol and 9.37 L deionized water. A mild odor of ethyl propionate was noted, but no phase separation was seen. The pH was adjusted to 8.8 with ammonium hydroxide, and white solids slowly precipitated. The mixture was chilled to approximately 9° C. and filtered with vacuum. The solids were washed twice on the filter with 2 L deionized water and reslurried in 10 L at room temperature. They were refiltered and again washed twice with 2 L deionized water. The solids were air-dried and analyzed by NMR, which showed no ethanol remaining. The combined yield was 6.12 kg, 102% of theory. m.p. 73.8°-75.1° C.

EXAMPLE 3

A 100-g sample of d-propoxyphene prepared as in Example 1 was dissolved in 481 mL ethyl acetate. 26.0 mL methanolic HCl (11.7M) was added. The mixture was warmed to between 30° and 40° C. The mixture then slowly crystallized. It was cooled to below 5° C. and filtered. The crystals were washed with 50 mL cold ethyl acetate. The yield was 79.3 g (72%).

Unconverted free base was recovered from the ethyl acetate filtrate by twice extracting with 100 mL of water acidified with 5 drops conc. HCl. The aqueous extracts were combined, and the remaining ethyl acetate was removed by blowing air over the solution. When the ethyl acetate was completely removed, the pH was raised to 9.0 by adding ammonium hydroxide; solids formed that were filtered, washed and dried. 25.3 g d-propoxyphene were recovered. The total yield of salt and recovered free base was 94.5%.

EXAMPLE 4

A 40-g sample of d-propoxyphene prepared as in Example 2 was slurried in 169 mL deionized water with stirring and 10.9 mL conc. HCl were added.

Seventy mL ethanol were added; then 30.15 g sodium napsylate were added with stirring. The resulting slurry was heated to between 50° and 60° C. until a solution was obtained. The solution was filtered while hot and then allowed to cool, with stirring. Crystallization started on cooling. The solution was then chilled to less than 5° C. and filtered. The solids were washed with 210 mL deionized water and then reslurried in 195 mL deionized water. The slurry was stirred for 15 minutes, then filtered. The solids were again washed with 210 mL deionized water, collected, and dried overnight at 50°-60° C. The yield was 63.6 g (95.4 percent of theory).

What is claimed is:

1. A method of preparing d-propoxyphene comprising
   (a) dissolving d-oxyphene in propionic anhydride solvent so as to form a solution of said d-oxyphene in said propionic anhydride, which solution is substantially free of other non-aqueous solvent;
   (b) reacting said d-oxyphene with said propionic anhydride in said solution under acylating conditions at a temperature of from about 70° to about 80° C. so as to form d-propoxyphene; and
   (c) thereafter isolating d-propoxyphene from the solution.

2. A method according to claim 1, wherein the amount of propionic anhydride is used in molar excess to the amount of d-oxyphene.

3. The method according to claim 2, wherein the amount of propionic anhydride used is in a ratio of 2.2 to 2.3 moles per mole of d-oxyphene.

4. The method according to claim 1, wherein said reaction step is carried out under a nitrogen atmosphere.

5. A method according to claim 1, wherein said isolation step is carried out by precipitation from water or an ethanol-water mixture having a pH of about 8.8 or above.

6. A method according to claim 5, wherein said pH is achieved by addition of a sufficient amount of ammonium hydroxide, sodium hydroxide, or potassium hydroxide.

7. A method according to claim 5, wherein said precipitation uses an ethanol-water mixture in a ratio ranging from about 90 parts ethanol to about 10 parts water to about 10 parts ethanol to about 90 parts water, on a volume basis.

8. The method of claim 7, wherein said mixture of ethanol and water is in a ratio of about 25 parts ethanol to about 75 parts water, on a volume basis.

9. The method of claim 7, wherein said mixture of ethanol and water is in a ration of about 50 parts ethanol to about 50 parts water, on a volume basis.

10. A method according to claim 1, additionally comprising adding a catalytic amount of water to said solution of d-oxyphene in propionic anhydride.

11. A method according to claim 10, wherein propionic anhydride is used in molar excess to d-oxyphene.

12. A method according to claim 11, wherein propionic anhydride is used in a ratio of 2.2 to 2.3 moles per mole of d-oxyphene.

13. A method according to claim 10, wherein said reaction step is carried out under a nitrogen atmosphere.

14. A method according to claim 12, wherein said reaction step is carried out at temperatures from about 70° to about 80° C.

15. A method according to claim 10, wherein said isolation step is carried out by precipitation from water or an ethanol-water mixture having a pH of about 8.8 or above.

16. A method according to claim 15, wherein said pH is achieved by addition of sufficient amount of ammonium hydroxide, sodium hydroxide, or potassium hydroxide.

17. A method according to claim 15, wherein said precipitation uses an ethanol-water mixture in ratio ranging from about 90 parts ethanol to about 10 parts water to about 10 parts ethanol to about 90 parts water, on a volume basis.

18. The method of claim 17, wherein said mixture of ethanol and water is in a ratio of about 25 parts ethanol to about 75 parts water, on a volume basis.

19. The method of claim 17, wherein said mixture of ethanol and water is in a ratio of about 50 parts ethanol to about 50 parts water, on a volume basis.

20. A method for preparing the hydrochloride salt of d-propoxyphene comprising
 (a) preparing and isolating free base d-propoxyphene by the method of claim 1;
 (b) drying isolated d-propoxyphene to substantial dryness;
 (c) dissolving said d-propoxyphene in ethyl acetate;
 (d) adding methanolic hydrogen chloride; and
 (e) isolating d-propoxyphene hydrochloride.

21. A method for preparing the naphthalene sulfonate salt of d-propoxyphene comprising
 (a) preparing and isolating free base d-propoxyphene by the method of claim 1;
 (b) adding hydrochloric acid to said isolated d-propoxyphene;
 (c) adding sodium naphthalene sulfonate; and
 (d) isolating d-propoxyphene naphthalene sulfonate.

22. A method of preparing d-proxyphene comprising
 (a) dissolving d-oxyphene in propionic anhydride solvent so as to form a solution of said d-oxyphene in said propionic anhydride, which solution is substantially free of other non-aqueous solvent;
 (b) reacting said d-oxyphene with said propionic anhydride in said solution under acylating conditions at a temperature within the range of between 50° C. to about 120° C., but no higher than 90° C., so as to form d-propoxyphene; and
 (c) thereafter isolating d-propoxyphene from the solution.

* * * * *

UNITED STATES PATENT AND TRADEMARK OFFICE
CERTIFICATE OF CORRECTION

PATENT NO. : 5,312,970
DATED      : May 17, 1994
INVENTOR(S) : John R. Duchek

It is certified that error appears in the above-indentified patent and that said Letters Patent is hereby corrected as shown below:

Col. 7, line 24, "12" should be -- 10 --.

Signed and Sealed this

Ninth Day of August, 1994

BRUCE LEHMAN

Attest:

Attesting Officer

Commissioner of Patents and Trademarks